ical Patent

(12) United States Patent
Howgill

(10) Patent No.: US 10,596,333 B2
(45) Date of Patent: Mar. 24, 2020

(54) DOSE INDICATOR FOR A METERED DOSE INHALER

(71) Applicant: 3M INNOVATIVE PROPERTIES COMPANY, St. Paul, MN (US)

(72) Inventor: Stephen J. Howgill, Thurcaston (GB)

(73) Assignee: 3M Innovative Properties Company, Saint Paul, MN (US)

( * ) Notice: Subject to any disclaimer, the term of this patent is extended or adjusted under 35 U.S.C. 154(b) by 685 days.

(21) Appl. No.: 15/301,362

(22) PCT Filed: Mar. 31, 2015

(86) PCT No.: PCT/US2015/023534
§ 371 (c)(1),
(2) Date: Sep. 30, 2016

(87) PCT Pub. No.: WO2015/153570
PCT Pub. Date: Oct. 8, 2015

(65) Prior Publication Data
US 2017/0173280 A1 Jun. 22, 2017

(30) Foreign Application Priority Data
Apr. 3, 2014 (GB) .................................. 1406046.1

(51) Int. Cl.
*A61M 15/00* (2006.01)
*G06M 1/04* (2006.01)
(52) U.S. Cl.
CPC .......... *A61M 15/0068* (2014.02); *G06M 1/04* (2013.01); *G06M 1/041* (2013.01); *G06M 1/045* (2013.01)
(58) Field of Classification Search
CPC .......... A61M 15/0021; A61M 15/0026; A61M 15/0045; A61M 15/0051; A61M 15/0065;
(Continued)

(56) References Cited

U.S. PATENT DOCUMENTS 5,063,285 A 11/1991 Curry
6,179,118 B1 * 1/2001 Garrill ................ A61M 15/009
206/204

(Continued)

FOREIGN PATENT DOCUMENTS

WO  WO 1998-52634   11/1998
WO  WO 2005-102430  11/2005
(Continued)

OTHER PUBLICATIONS

International Search Report for PCT International Application No. PCT/US2015/023534, dated Jun. 25, 2015, 4 pages.

*Primary Examiner* — Annette Dixon
(74) *Attorney, Agent, or Firm* — 3M Innovative Properties Company

(57) ABSTRACT

The present disclosure relates to a dose indicator comprising, a chassis comprising a chassis frame and a displacement portion, an indexable first display unit, mountable on the chassis, the first display unit being indexable about a first display axis, the indexable first display unit comprising a plurality of indexing teeth, a first display non-return arm, and a drive pawl connected at its proximal part to the displacement portion, the drive pawl comprising a socket at its distal part, the socket being adapted to engage an indexing tooth of the first display unit during indexing. The disclosure further relates to an actuator for an inhaler, wherein the actuator comprises a dose indicator as described above. The present disclosure is also directed to an inhaler comprising such actuator.

35 Claims, 8 Drawing Sheets

(58) Field of Classification Search
CPC .......... A61M 15/0068; A61M 15/0071; A61M 15/0073; A61M 15/0075; A61M 15/0076; A61M 15/008; A61M 15/0081; A61M 15/009; A61M 2202/064; A61M 2205/12; A61M 2205/3306; A61M 2205/3368; A61M 2205/3375; A61M 2205/581; A61M 2205/82; G06M 1/04; G06M 1/041; G06M 1/042; G06M 1/045; G06M 1/083; G06M 1/163; G06M 1/166; G06M 1/241; G06M 1/248; G09F 11/23
See application file for complete search history.

(56) References Cited

U.S. PATENT DOCUMENTS

| | | | |
|---|---|---|---|
| 6,446,627 B1* | 9/2002 | Bowman | A61M 15/009 128/200.23 |
| 6,752,153 B1 | 6/2004 | Eckert | |
| 8,141,550 B2* | 3/2012 | Lawrence | A61M 15/009 128/200.14 |
| 10,092,714 B2* | 10/2018 | Stuart | G06M 1/041 |
| 2006/0060192 A1* | 3/2006 | Lu | A61M 15/009 128/200.23 |
| 2007/0241025 A1* | 10/2007 | Parkes | A61M 15/0065 206/534 |
| 2009/0173346 A1* | 7/2009 | Stuart | A61M 15/009 128/203.12 |

FOREIGN PATENT DOCUMENTS

| | | |
|---|---|---|
| WO | WO 2006-110080 | 10/2006 |
| WO | WO 2007-124406 | 11/2007 |
| WO | WO 2011-071788 | 6/2011 |
| WO | WO 2013-110927 | 8/2013 |
| WO | WO 2014-039367 | 3/2014 |
| WO | WO 2015-006292 | 1/2015 |
| WO | WO 2015-153624 | 10/2015 |

* cited by examiner

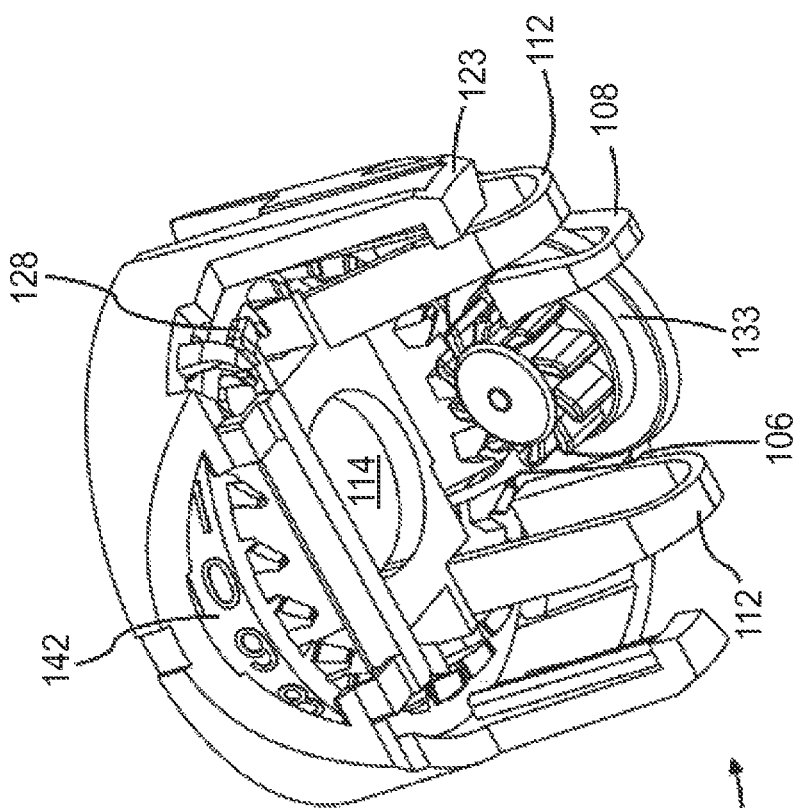
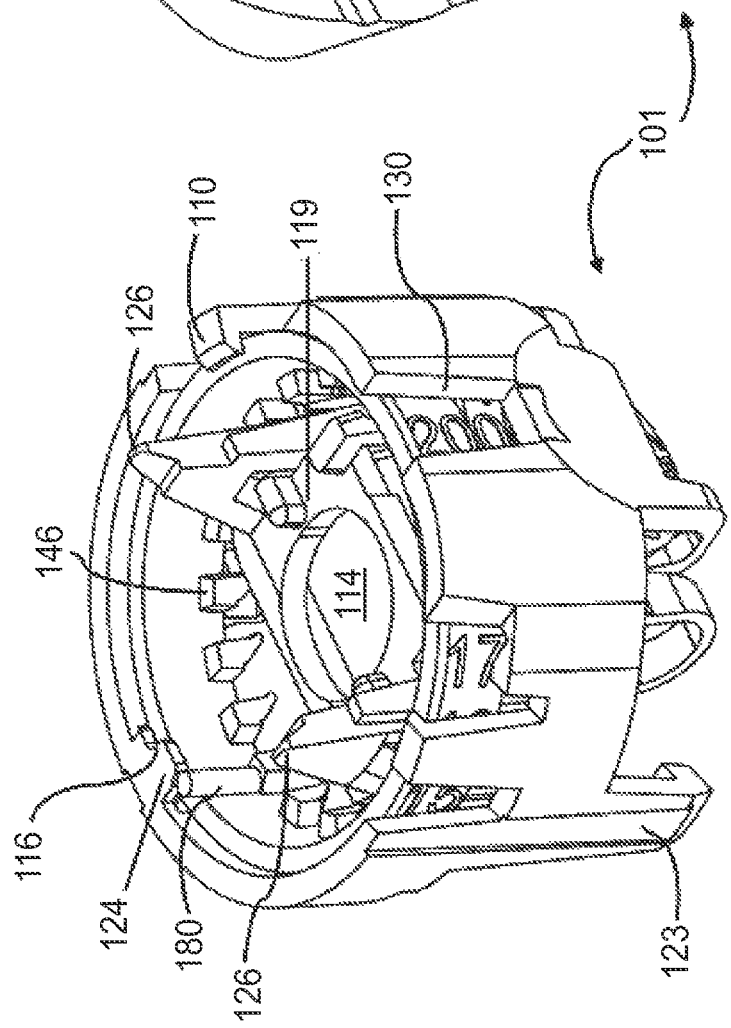

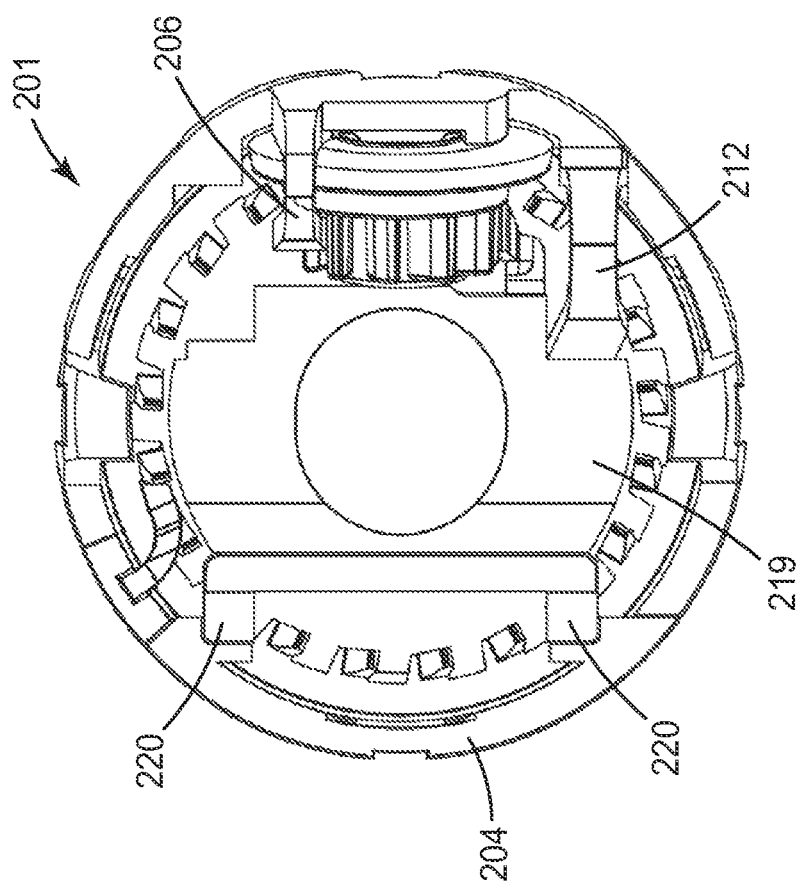
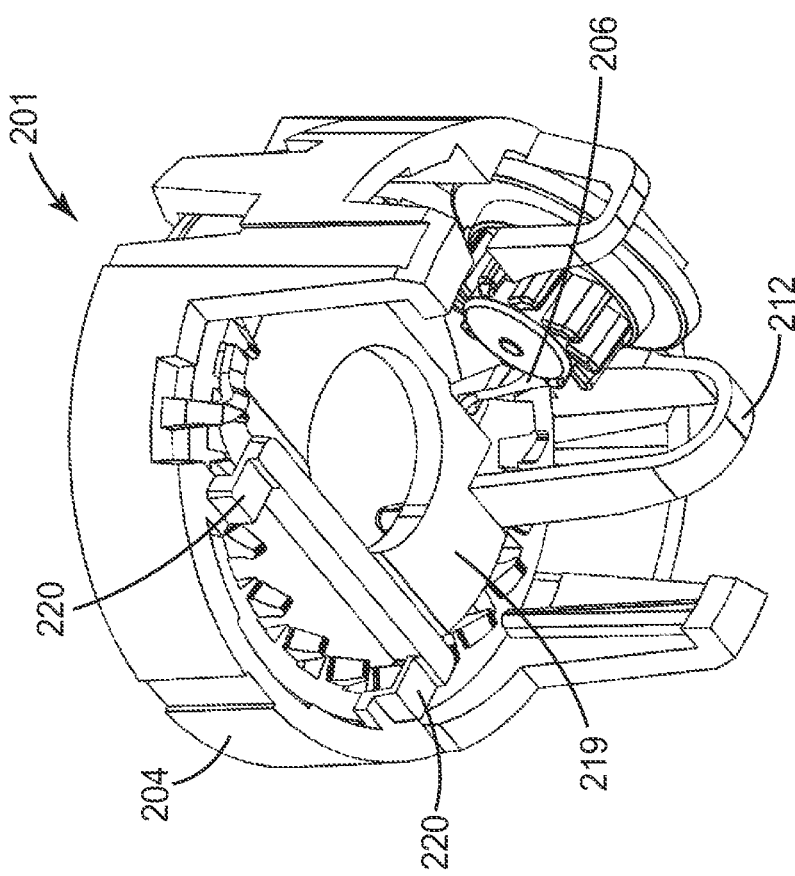

DOSE INDICATOR FOR A METERED DOSE INHALER

CROSS-REFERENCE TO RELATED APPLICATIONS

This application is a national stage filing under 35 U.S.C. 371 of PCT/US2015/023534, filed Mar. 31, 2015, which claims the benefit of UK Application No. 1406046.1, filed Apr. 3, 2014, the disclosures of which are incorporated by reference in their entirety herein.

FIELD OF THE INVENTION

The present specification relates to dose indicators or dose counters, and more particularly to dose indicators or dose counters for pressurised metered dose inhaler (pMDI) devices. The present invention also relates to actuators comprising such dose indicators/counters and to inhalers comprising such actuators.

BACKGROUND OF THE INVENTION

Patients who need to use inhalers, such as pMDI devices, need to monitor their inhaler usage, and regulators of medicines have begun to require that some method of dose counting is included into the inhaler. Dose counters (providing a precise count of the number of doses remaining) and dose indicators (providing an indication of the number of doses remaining) for inhalers are known.

In most dose counters and dose indicators, the display is indexed each time the inhaler device is used and a dose is delivered, e.g. from a metering valve of the inhaler where the inhaler is a pMDI. It is particularly important that dose counters and dose indicators do not undercount the number of dispensed doses as, in extreme cases, the patient may rely on the display shown on the pMDI device to receive life-saving medication. Note that the term 'dose', as used herein, includes individual deliveries of medication formulation that in multiple make up a single therapeutic dose.

In dose counters or dose indicators, it may be acceptable for advancement of the display to be triggered (initiated) before or after the dose has been delivered, provided that the patient cannot dispense a dose without triggering it. Many dose counters and/or dose indicators are complex, requiring a number of small mechanical parts, which may increase cost, may lead to difficulties in assembly, and may require tight dimensional tolerances.

DESCRIPTION OF RELATED ART

WO-A-2011/071788 discloses dose counters for dispensers and in particular dose counters for use with metered dose inhalers.

U.S. Pat. No. 6,752,153 discloses an inhaler for aerosolization of medicament with a dose counter. The dosage counter has a first and a second counting ring and a coupling device that connects the counting rings.

WO-A-2013/110927 discloses mechanisms by which operation of dry powder inhalers is disabled after a predetermined number of actuations of the device.

WO-A-98/52634 discloses a dosing device and in particular relates to dosing devices for drug delivery such as injectors and inhalers and a mechanism for use in such devices.

WO-A-2006/110080 discloses inhaler device counters, and in particular a counter mechanism for such.

BRIEF SUMMARY OF THE INVENTION

It is an aim of the present invention to provide a dose counter or dose indicator that has a relatively small number of parts and is reliable in use.

In this specification, the term "dose indicator" is intended to refer to both dose counter devices and dose indicator devices.

In a first aspect, there is provided a dose indicator comprising, a chassis comprising a chassis frame and a displacement portion, an indexable first display unit, mountable (or mounted) on the chassis, the first display unit being indexable about a first display axis, the indexable first display unit comprising a plurality of indexing teeth, a first display non-return device, and a drive pawl connected at its proximal part to the displacement portion, the drive pawl comprising a socket at its distal part, the socket being adapted to engage an indexing tooth of the first display unit during indexing.

The first display non-return arm will usually be adapted to resiliently engage one or more non-return teeth on the first display unit. The non-return teeth may be the indexing teeth.

This is advantageous because it provides a dose indicator/counter that has a small number of components yet is effective, reliable and compact. In particular, the socket part of the drive pawl partially surrounds the engaging part of the tooth and ensures good continual engagement during actuation.

This advantage is particularly important in dose indicators because of their small size and low mass components.

Furthermore, the invention allows the provision of a cheap, simple and reliable dose-by-dose counter that is capable of counting 200 doses or inhaler actuations ('puffs'). It may count down from 200 to 0 and is able to fit within a pMDI actuator of similar shape and comparable size to existing actuators.

The distal part of the drive pawl usually comprises jaws, the inner surfaces of which define the socket.

In most embodiments, the distal part comprises an outer surface adapted to engage a subsequent indexing tooth during resetting of the pawl after indexing. The part of the outer surface that engages the subsequent tooth is the resetting surface of the pawl. In embodiments that have a return means to reset the pawl, the return means exerts a return force on the proximal part of the pawl, and the drive pawl is resiliently displaced by a displacement force from the subsequent indexing tooth during resetting of the pawl after indexing. This is because the engagement of the resetting surface of the pawl with the subsequent tooth creates a lateral (i.e. generally radial, outwardly in this case, with respect to the units display unit) deflection of the distal end of the pawl. The extent and timing of the deflection of the distal end of the pawl is determined by the profile of the resetting surface, and can also depend on the shape and position of the subsequent tooth. A resolved component of the displacement force acts in the opposite direction to that of the return force, and hence tends to resist resetting of the dose indicator prior to its next cycle of operation.

Preferably, the drive pawl and indexing teeth are adapted so that the angle between the resetting surface and the trajectory of the proximal part of the drive pawl during resetting (the displacement angle) is small. This is advantageous because a relatively small displacement angle results in a small resistance opposing the return force improving consistency of counting and resetting of the dose indicator/counter.

Furthermore, the drive pawl and indexing teeth are preferably adapted so that the lateral deflection of the pawl occurs early in the return travel. This enables resetting under the influence of the springs that provide the return means while the pawl is further from its rest position and where the return springs have a higher return force. Consequently the displacement work may be optimized (i.e. excessive peak resistive forces avoided) over a greater resetting distance, improving the device robustness and consistency of counting. By appropriate design, the return force may be arranged to always exceed the resolved resistive force component that acts in the opposite direction to the return force. The displacement angle is preferably 45 degrees or below, more preferably 40 degrees or below, and most preferably 35 degrees or below. Usually the displacement angle will be in the range 45 degrees to 3 degrees, more usually 40 degrees to 5 degrees and most usually 35 degrees to 7 degrees. The lower limit for each of these ranges of displacement angle may by 8 degrees, 9 degrees or 10 degrees.

Usually, each indexing tooth comprises a pawl engagement portion adapted to engage the socket. Preferably the pawl engagement portion is curved with a small radius of curvature of usually 5 mm or less, preferably 2 mm or less, more preferably 1 mm or less, most preferably 0.7 mm or less.

In many embodiments of dose indicators according to the present invention there further comprises an indexable second display unit indexable about a second display axis, the second display axis being transverse to the first display axis. This is advantageous because it enables a higher maximum dose count to be conveniently achieved.

Generally, the first display unit and/or the second display unit will be substantially circular in a cross-section (usually a cross section transverse, preferably generally orthogonal, to the first and/or second display axis respectively) and will be rotatably indexable about the first display axis and/or about the second display axis respectively. The term "substantially circular" in this context includes annular or disc-shaped embodiments and polygonal shapes with at least five sides.

Preferably, the chassis is moulded as a unitary piece. This is advantageous because it enables the reduction of the number of parts of the dose indicator, with consequent benefits of cost and simplicity of assembly.

It is preferred if the drive pawl is integrally comprised in the displacement portion.

In most embodiments, the displacement portion may be mounted to the chassis frame by hinge means, preferably at least one hinge. The proximal part of the drive pawl will usually be located on the displacement portion at a position remote from the hinge means or hinges, preferably at a position of the displacement portion distal to the hinge means or hinges.

The hinge means (e.g. hinge or hinges) may generally be any connecting portion including such that allows restricted but controlled relative movement of the displacement portion and the chassis frame, including relative rotational and/or translational movement.

Usually, the displacement portion will be adapted to be displaced along a displacement path that is preferably at least partly transverse to the first display axis. It is preferred if the displacement path is at least partly arcuate. This may be achieved, for example, if the drive pawl is located on the displacement portion at a position remote from the hinge or hinges, preferably at a position distal to the hinge or hinges. The hinge or hinges may also be configured for substantially pivotal (rotational) movement of the displacement portion.

Usually, the displacement portion will comprise at least one press member that acts as an interference portion for interference with the inhaler valve during actuation. The press member or members may for example be a press knuckle or press knuckles. It is advantageous if the contact points (e.g. press knuckles) between the valve and the displacement portion comprise multiple points that are radially in different directions from the valve stem, as this helps to compensate for effects of the patient tilting the pMDI medicament-containing canister slightly during actuation. Thus, preferably there are two or more contact points (e.g. press knuckles) distributed on the displacement portion.

The first display non-return device will usually be a first display non-return means and will often be at least partly located on the chassis frame. The non-return device preferably comprises a non-return arm adapted to interact with one or more detents (which would usually be one or more indexing teeth other than the indexing tooth or indexing teeth currently being engaged by the drive pawl) on the first display unit.

The chassis preferably further comprises at least one return means. The return means will usually comprise at least one spring. Preferably, the at least one spring comprises a leaf spring, preferably a curved leaf spring. The at least one return means (preferably a curved leaf spring) will usually directly or indirectly connect the displacement portion and chassis frame, preferably at a position remote from the hinge or hinges.

Usually, the first and/or the second display unit will be adapted to index through between 5 and 25 indicia, preferably 8 to 12 indicia.

The dose indicator may comprise a first display unit mounting means for mounting the display unit on the chassis frame so that it is indexable about the first display axis.

The internal profile of the first display unit may include an axle bearing and the chassis may include an axle ('first display unit axle') with an external profile designed to engage closely with the axle bearing to allow relative rotational movement without wobble. This may be achieved by close circumferential engagement of the internal profile of the first display unit axle bearing and the external profile of the first display unit axle over most of the circumference corresponding to positions on the first display unit axle that are axially separated by some distance. This distance is preferably greater than the thickness of the portion of the units display unit that bears indicia.

The first display unit axle may be substantially cylindrical, or it may have cylindrical sections of different diameter, for example with the section closer to the first display unit's indicia having the larger diameter. The first display unit axle may have a lead-in surface at the distal end to facilitate placing of the first display unit. This first display unit axle may be configured to hold the first display unit in position and to prevent its axial translation along the first display unit axle, e.g. by the provision of circumferential detents in the first display unit axle bearing.

Usually, in embodiments of the invention, the first display unit is a units display unit.

Preferably, the second display unit is a tens display unit.

In preferred embodiments the first display unit comprises a drive arm adapted to index the second display unit. This is particularly suited to embodiments in which the second display unit is a tens display unit.

In some embodiments the first display unit has a substantially circular or annular cross section, preferably substantially circular and preferably a cross section transverse (more preferably substantially orthogonal) to the first display axis.

In some embodiments the second display unit has a substantially circular or annular cross section, more preferably a substantially annular cross section. It is preferred if the cross section is transverse (more preferably substantially orthogonal) to the second display axis.

In preferred embodiments, the first and/or the second display unit comprises a zero stop means. It is particularly preferred that the second display unit comprises a zero stop means to stop the second display unit from advancing beyond the zero count of the second display unit (e.g. tens display unit) corresponding to a nearly empty inhaler, and the second display unit is preferably further configured to prevent indexing of the first display unit beyond the ensuing zero units count. This configuration of the stop means may be achieved by using positive engagement between the first (e.g. units) display unit and the second (e.g. tens) display unit. In embodiments where the first and/or the second display unit comprises a zero stop means, the drive member may be configured to deflect or collapse to allow continued use of the inhaler after the displayed overall count has reached zero.

Preferably, the zero stop means interacts with a stop feature, more preferably a stop arm, located on the chassis.

In any embodiments, advantageously the chassis comprises polyoxymethylene (i.e. POM, acetal). The polyoxymethylene is preferably in homopolymer form.

In a second aspect, the invention provides an actuator for an inhaler, the actuator comprising a dose indicator as discussed in the first aspect.

In a third aspect, the invention provides an inhaler comprising an actuator as discussed in the second aspect.

The dose indicator of the present invention is of simple construction, whilst being robust and reliable in its indication of doses. It is suitable for use in a pressurized metered dose inhaler (pMDI) or other dispensing devices (e.g. dry powder inhalers, aqueous pump dispensers) to indicate usage (e.g. number of doses used or number of doses remaining) by means of numbers and/or coloured regions or other indicia in its display. Typically doses are counted downwards, and an indication of when the inhaler canister needs to be replaced may be provided in addition to an indication of the number of doses that have been dispensed.

When adapted for a pMDI, the dose indicator may be of a suitable size and configuration to fit into existing inhaler actuator designs, including breath actuated actuators or actuators with breath coordination means incorporated, without appreciable changes to the dimensions or shape of the existing actuator design. Actuators will typically be provided with a window for viewing the dose indication or count.

So that the present specification may be more completely understood, reference is made to the accompanying drawings in which like elements are given like reference numerals (with the addition of 100 to the numerals of the second embodiment illustrated):

BRIEF DESCRIPTION OF THE DRAWINGS

FIGS. 7A and 7B show different perspective views of the dose indicator of FIGS. 3 to 6.

FIGS. 8A and 8B show different perspective views of a third exemplary dose indicator.

DETAILED DESCRIPTION OF THE INVENTION

Certain embodiments of this invention relate to a two-component (with an optional third component) dose indicator for a pMDI. The indicator is designed to be indexed by the displacement generated when a patient actuates a pMDI valve.

Figure 1:
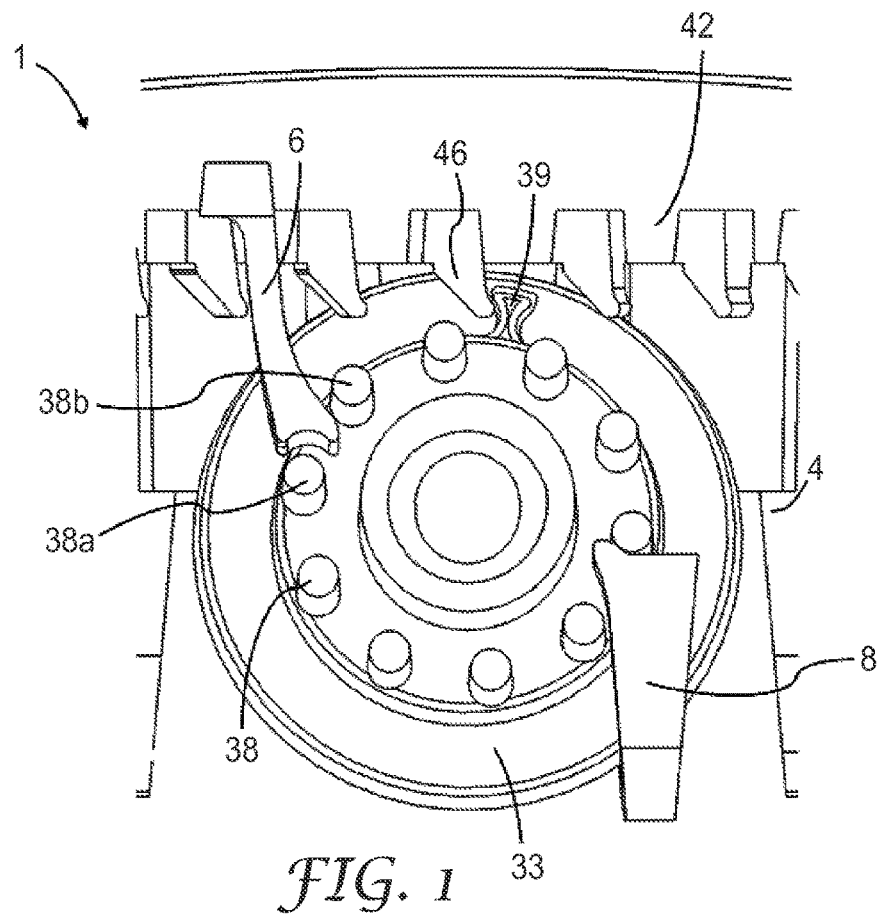
FIG. 1 shows a side perspective view of part of an exemplary dose indicator.
Figure 2:
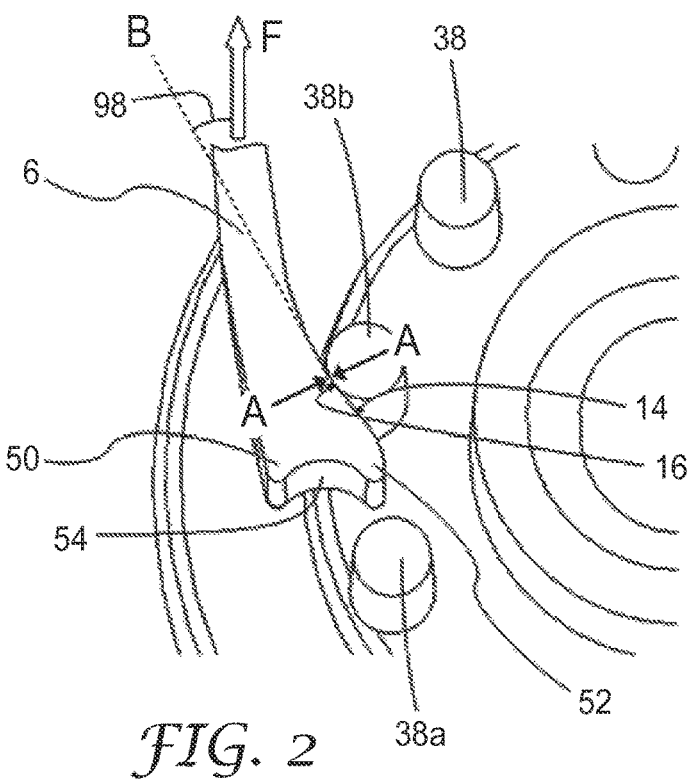
FIG. 2 shows a detail of the interaction between the drive pawl and indexing teeth in the dose indicator of FIG. 1.

In the embodiment illustrated in FIGS. 1 and 2, a dose indicator in the form of a dose counter 1 comprises a dose-by-dose counter for a pMDI that is capable of being configured to count down from 200 to 0 which comprises a chassis, a units display unit 33 and an optional tens display unit 42. The dose counter 1 can be inserted into a standard pMDI actuator.

Figure 3:
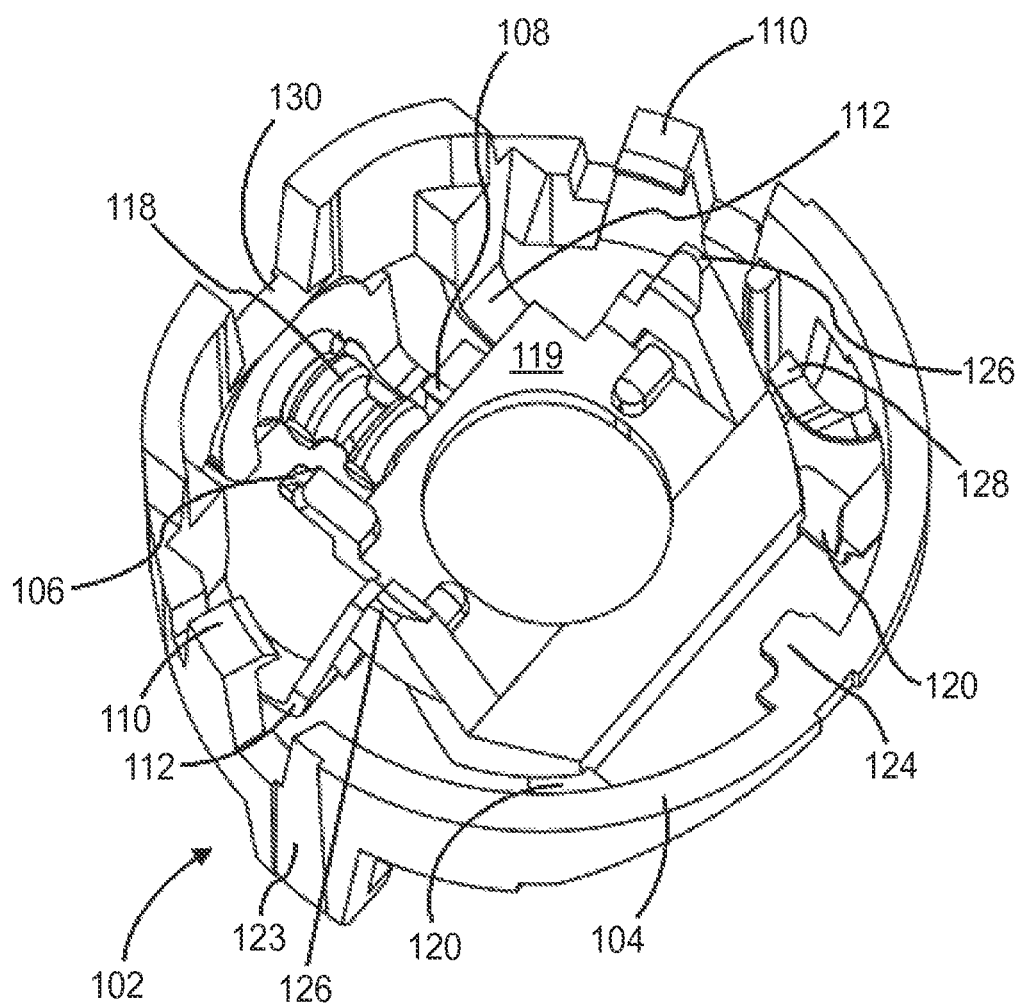
FIG. 3 shows a top perspective view of a chassis of a second exemplary dose indicator.

The dose counter has a chassis that is similar to that of the second embodiment (where it is shown as 102), shown in FIG. 3. The chassis has a generally annular form, designed to fit snugly into an inhaler actuator to provide support and to prevent deformation in use. FIG. 3 illustrates how a drive pawl 106 and a non-return arm 108 are integrally formed with the chassis frame 104; the corresponding components of the first embodiment (6, 8 and 4) are constructed in the same way. Optionally the support may be enhanced by one or more ledges on the actuator for seating a horizontal surface of the chassis, or ribs/grooves to prevent deformation and relative rotation of the chassis frame in the actuator. The chassis incorporates a number of features including springs, hinges and indexing features that are used to actuate and reset the device. The features are formed integrally (i.e. moulded in a unitary piece) with the chassis.

As seen in FIG. 1 and FIG. 2, the dose counter 1 comprises a units display unit 33 that comprises a series of units display unit indexing teeth 38. The indexing teeth are peg-like of generally cylindrical shape. A drive pawl 6 formed integrally with the chassis contacts the indexing teeth 38 and indexes the teeth when the displacement portion of the chassis is pressed against by a valve of a medicament canister pressing downwards on indexing knuckles 26 (not visible in FIG. 1: see FIG. 3) on the top side of the chassis. The drive pawl 6 has at its distal part jaws 50, 52 which define a socket 54. The socket is adapted to closely engage with the surface of the indexing teeth 38. When pressed downwards, a displacement portion in the form of a displacement plate 19 (see FIG. 3) of the chassis moves downwards and hinges 20 (see FIG. 3), integrally formed with the chassis frame 4 and displacement plate 19, deform. Spring arms 12, also integrally formed with the chassis frame 4 and displacement plate 19, return the chassis 2 to its original position after indexing.

In FIG. 1, a non-return arm 8, also formed integrally with the chassis, is shown as contacting the units display unit indexing teeth 38 on the opposite side to the drive pawl 6. This non-return arm prevents backwards movement of the units display unit 33 and helps urge it into a count-indicating position in which the display indicia are aligned with a window or gap in the chassis.

The dose counter 1 also comprises an optional tens display unit 42 in the form of a ring with tens display unit indexing teeth 46 indexed by a tens display unit drive tooth 39 on the units display unit, and generally prevented from backwards movement by the tens display unit non-return arm 28 (see FIG. 3).

FIG. 2 shows a detailed view of the drive pawl 6 and indexing teeth 38. When displaced, the drive pawl 6 engages and displaces the driven (peg-like) indexing tooth 38a. On its resilient return to reset for the next stroke/actuation cycle of the dose counter 1, the outer (resetting) surface 14 of the drive pawl 6 rides over the adjacent surface of the subsequent indexing tooth 38b. There is close engagement between the outer surface 14 and the outer surface 16 of the indexing tooth 38b, and contact at points A-A. The surfaces 14, 16 are so adapted that the displacement angle 98 between the line B along the tangent of the point of contact A-A and the line F along the direction of return of the drive pawl 6 is relatively small so that there is less resistance to the return force. Also, because the lateral deflection of the drive pawl 6 occurs early in the return travel, the resultant resistive forces are encountered when the drive pawl 6 is relatively far from its rest position, i.e. they occur where the return springs still provide a higher return force. Consequently, the device reliability is improved and the work required to deflect the pawl outwards may be smoothed over a greater resetting distance without the creation of excessive peak resistive forces.

The outer jaw 52 of the distal end of the pawl, when partially engaged with the surface of the driven tooth 38a, serves to pull the pawl 6 further into engagement (i.e. laterally towards the centre of the units display unit) with the tooth during the driving part of the cycle. This helps to increase the contact between the pawl 6 and the driven tooth 38a, thereby ensuring reliable engagement between them. The drive pawl resetting surface 14 has a shape that serves to reduce the lateral contact force between the pawl 6 and the next tooth 38b on the return stroke. In this way, both reliable driving engagement is ensured and reliable low resistive forces during resetting are also obtained.

FIG. 3 shows the chassis 102 of a second exemplary dose counter 101. In addition to features analogous to those visible in FIG. 1, the chassis 102 comprises indexing knuckles 126 that, in use, are contacted by the valve of a medicament canister when it is displaced downwards to actuate the metered dose valve to dispense a metered dose. The indexing knuckles 126 are carried on the displacement plate 119, which is anchored to the chassis frame 104 at one end by two hinges 120 and at the other end by two spring arms 112. An indexing element in the form of the drive pawl 106 is also attached to the displacement plate 119. The chassis 102 has a cut away portion 130 that provides a viewing path for display indicia, particularly when the chassis 102 is made of an opaque material. Below the cut away portion 130, an axle 118 extends inwardly. The chassis 102 is equipped with clips 110, a locating ledge 124 and a non-return arm 128. Legs 123 are provided on the chassis to secure the dose counter 101 precisely in an actuator body. Upon actuation the displacement plate 119 moves downwards and the hinges 120 deform. The spring arms 112 are resilient and resist displacement and return the displacement plate 119 to its original position after actuation. The two spring arms 112 have a long active length in order to reduce stress concentration. This is advantageous because it reduces the risk of creep in the springs over time. Having the spring arms 112 separate from the hinges 120 is also advantageous, as each feature is only required to perform a single function. In alternative embodiments, the hinges could be used to provide the spring force, but due to a short active spring length the stresses and strain in the hinges would be higher. In an alternative embodiment, the hinge means may be provided by one or more springs.

Due to the properties required for the spring arms and ratchets, the chassis 102 is preferably made from polyoxymethylene (also known as POM or acetal) or material with similar properties (high stiffness, low friction and good dimensional stability). Preferably the acetal is an acetal homopolymer. POM and materials with similar properties tend to be opaque, hence the need for a cut out portion in the chassis and corresponding window in the actuator body so that the indicia are visible.

The chassis component 102 has been designed such that it can be injection moulded without the requirement for a side action in the moulding tool. This is advantageous, as it reduces the capital cost of tooling and reduces the risk of flash on components.

Figure 4:
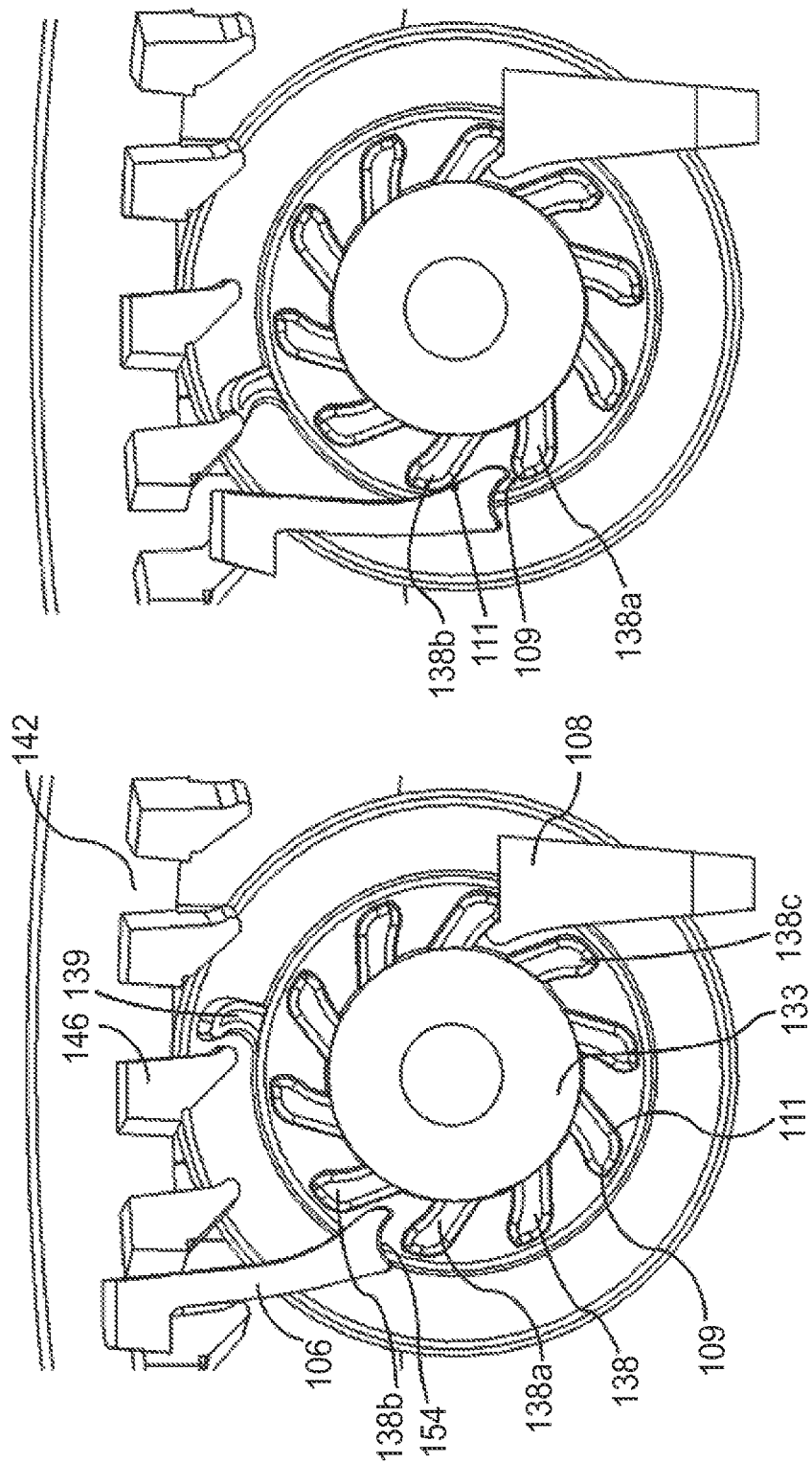
FIGS. 4A and 4B show partial side views of the exemplary dose indicator of FIG. 3, illustrating its operation.

FIGS. 4A and 4B show the second exemplary dose counter, FIG. 4A showing the dose counter at rest and FIG. 4B showing it part way through its actuation cycle. The dose counter in FIGS. 4A and 4B is similar in most of its components to that illustrated in FIGS. 1 and 2, but differs from that illustrated in FIGS. 1 and 2 in that the indexing teeth 138 are attached to the central boss of the units display unit 133 (rather than being of cylindrical form as in FIGS. 1 and 2). This is advantageous because it increases the robustness of the teeth.

During operation of the dose counter, upon actuation of the pMDI valve, the displacement plate (not visible in FIGS. 4A and 4B) bends at its hinges and displaces the drive pawl 106. The pawl 106 engages the units display unit indexing teeth 138 thereby advancing the display of the units display unit 133 by one count, and the drive pawl 106 then continues its travel as far as it continues to be driven by the user, up to the limit of travel of the pMDI valve. The socket 154 of the drive pawl 106 engages the pawl engaging portion 109 of indexing tooth 138a, which causes the rotation of the units display unit 133 by one count and which results in the non-return arm 108 being forced to flex and to ride over an indexing tooth 138c on the opposite side of the units display unit 133. The pawl engaging portion 109 of the indexing tooth is designed to fit snugly in the socket 154 to improve contact during engagement. Once indexed, the patient releases the canister to allow the dose counter 101 to reset under the influence of the spring force from the spring arms (112 in FIG. 3). The non-return arm 108 engages with the next of the indexing teeth 138c, thus preventing reverse rotation of the units display unit 133. Since the units display unit 133 is unable to rotate, the drive pawl 106 is forced to ride over the next of the units display unit indexing teeth 138b and return to its original rest position, resiliently riding over the outer surface 111 of the subsequent indexing tooth 138b. The outer surface 111 of the indexing tooth 138b is shaped to keep the drive pawl's displacement small, and to ensure that its deflection occurs early in its return travel. This avoids the risk of the force from the spring arms 112 being insufficient to ensure that the drive pawl 106 can pass over indexing tooth 138b during its return stroke. This ensures dose counter reliability.

On a tens count (e.g. for a displayed count changing from "190" to "189"), as the dose counter is indexed the rotation of the units display unit 133 causes a tens display unit drive tooth 139 (on the units display unit 133) to engage with one of the tens display unit indexing teeth 146 on the tens display unit 142.

Figure 5:
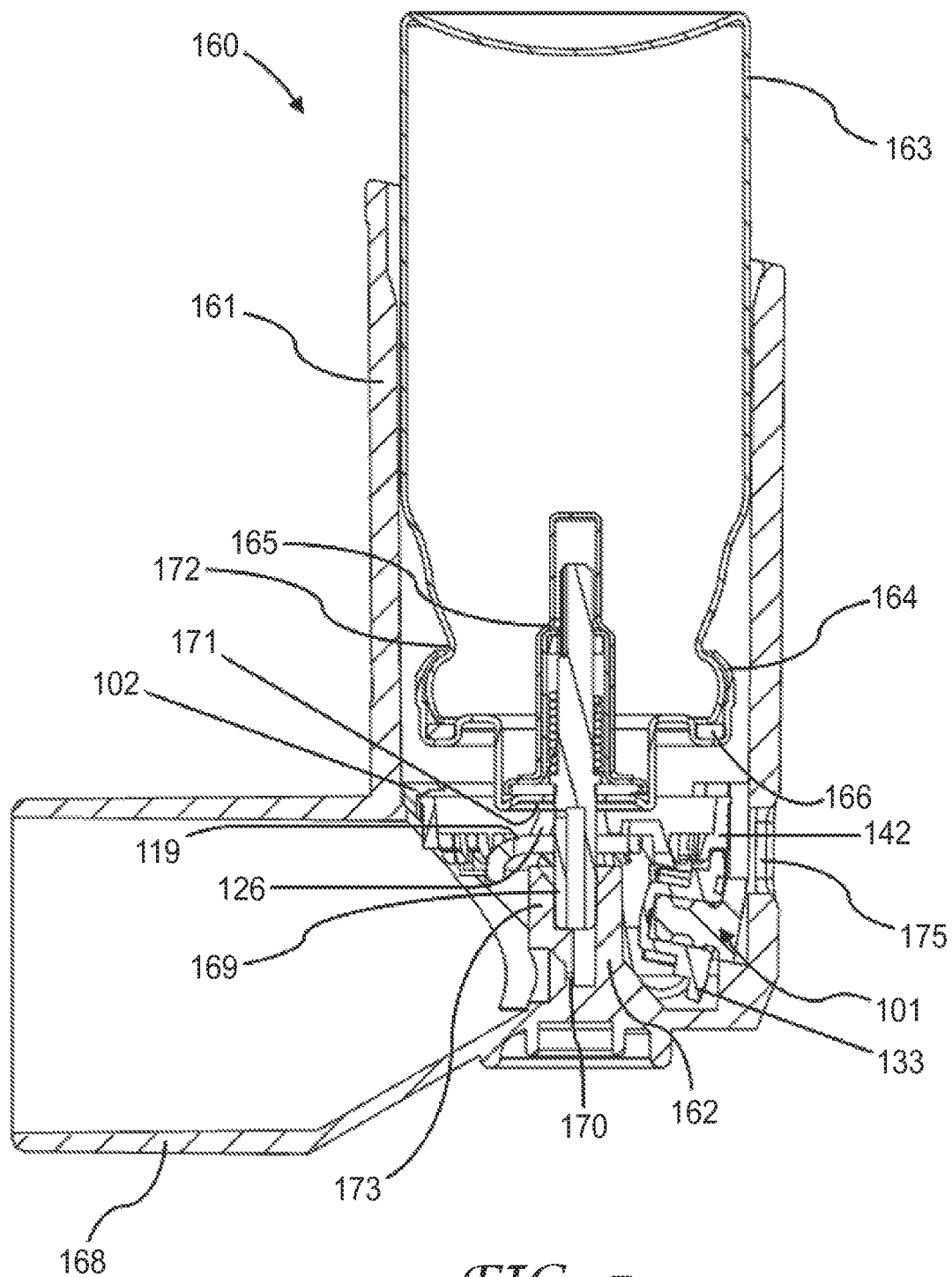
FIG. 5 shows a cross section through a pressurised metered dose inhaler incorporating a dose indicator as illustrated in FIGS. 3 and 4.

FIG. 5 shows a pressurised metered dose inhaler (pMDI) 160 comprising a canister 163 including a metered dose-dispensing valve 165 mounted via a ferrule 164 on to the neck of a vial 172 component of the canister 163 with an elastomeric gasket 166 to create a seal. The inhaler comprises an actuator 161 including a mouthpiece 168. (In an alternative form, suitable for nasal drug delivery, the actuator may comprise a nosepiece rather than a mouthpiece.) The canister 163 is placed within the actuator 161 by inserting the valve stem 169 of the valve 165, which protrudes outside the ferrule 164, into a stem socket 173 of a stem post 162 of the actuator 161. The valve stem 169 has a dispensing passage that allows for passage of substance from a metering chamber of the valve 165 out through the valve stem 169 and actuator mouthpiece 168 (or nosepiece) to the user. To actuate (fire) the valve 165 to deliver a dose of medicament formulation, the valve stem 169 is pushed inwardly relative to the aerosol container from its resting position, allowing formulation to pass from the canister through the valve 165 and through the actuator nozzle 170 and then out to the patient.

The actuator 161 has a dose counter 101, in the form of the dose counter shown in FIGS. 3 to 6, mounted around the stem post 162. An aperture 114 (see FIG. 7) in the displacement plate 119, larger than the cross-section of the stem post 162, allows for movement of the displacement plate over the stem post. The dose counter 101 has a units display unit 133, a tens display unit 142 and a chassis 102 with a displacement plate 119. During actuation, the canister 163 is pressed down by the user. As the canister 163 is pressed into the actuator 161, the ferrule face 171 surrounding the valve stem 169 contacts indexing knuckles 126 and displaces the displacement plate 119. The result is that the drive pawl (106; not visible in FIG. 5) indexes the units display unit 133. The patient is able to observe the displayed indicia via a window 175 in the actuator 161.

Figure 6:
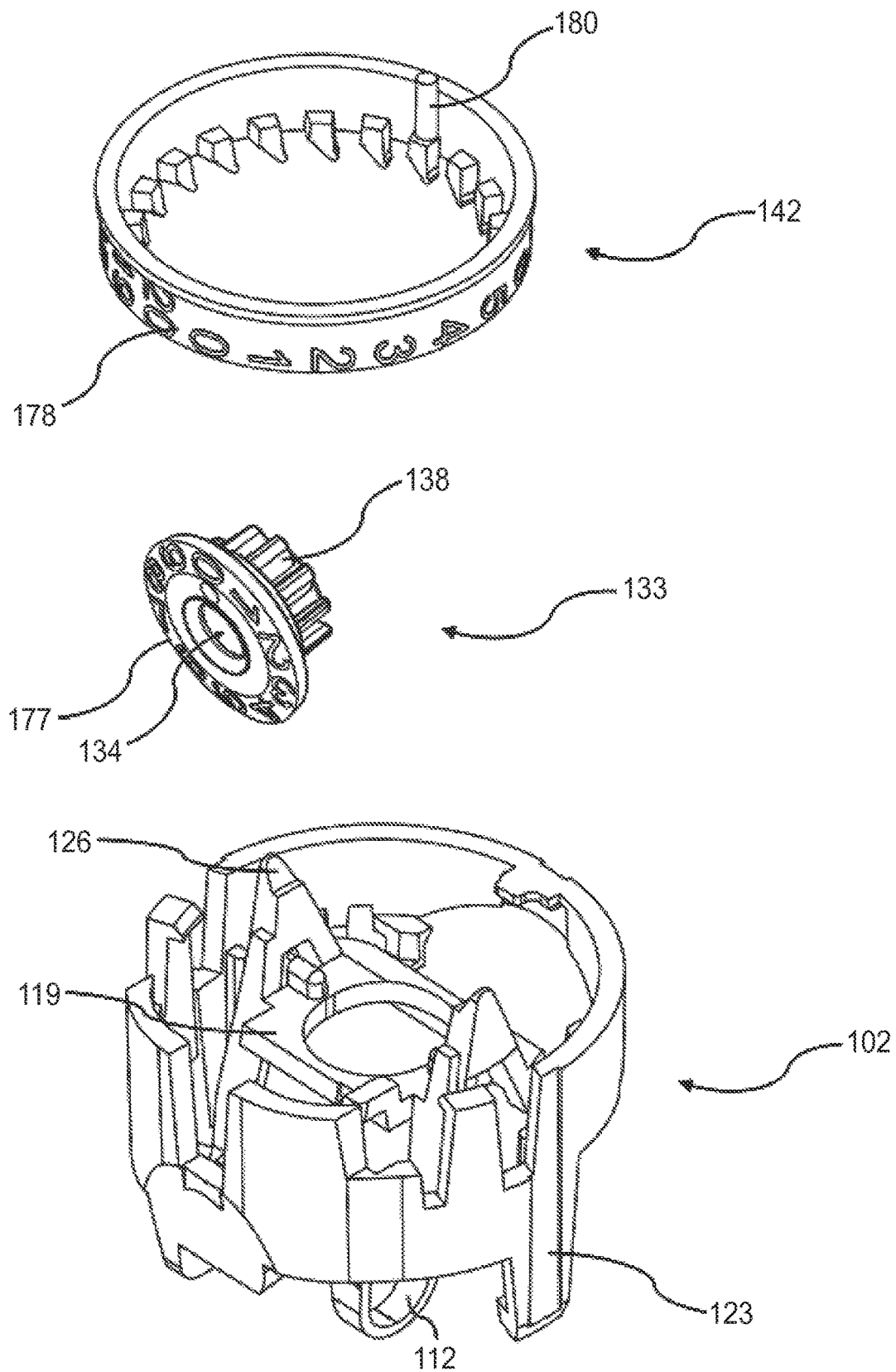
FIG. 6 shows an exploded perspective view of the components of the dose indicator of FIGS. 3 to 5.

FIG. 6 shows an exploded view of the dose counter 101, illustrating the three components: the chassis 102, the units display unit 133 and the tens display unit 142. The assembled dose counter 101 is shown (in two views) in FIGS. 7A and 7B.

The units display unit 133 is generally circular in external end view with an annular flange providing a units display unit display surface 177 bearing units indicia (e.g. ten numerals 0 to 9). On the internal side of the flange is a hollow boss surrounded by a series of units display unit indexing teeth 138. These teeth interact with the drive pawl 106 and also with the non-return arm 108 when the units display unit 133 is mounted on the chassis 102. In alternative embodiments, the indexing teeth with which the drive pawl interacts may comprise a different set of teeth from the set of indexing teeth with which the non-return arm interacts.

The axle bearing 134 of the units display unit 133 is mounted on the units display unit axle 118 of the chassis 102 (see FIG. 3). The internal profile of the units display unit 133, including axle bearing 134, and the external profile of the units display unit axle 118 are designed to engage closely to allow relative rotational movement without wobble. This may be achieved by close circumferential engagement of the internal profile of the units display unit 133 and the external profile of the units display unit axle 118 over most of the circumference corresponding to positions on the units display unit axle 118 that are axially separated by some distance. This distance is preferably greater than the thickness of the portion of the units display unit 133 that bears indicia. The units display unit axle 118 holds the units display unit 133 in position. The non-return arm 108 prevents the axial translation of the units display unit 133 along the units display unit axle 118, e.g. it prevents the units display unit 133 jumping off its mounting.

The units display unit 133 has been designed such that it can be injection moulded without the requirement for a side action in the moulding tool. This is advantageous, as it will reduce the capital cost of tooling and reduce the risk of flash on components.

The tens display unit 142 has the form of a hollow cylinder with a tens display unit display surface 178. Attached to parts of the lower and internal edge of the hollow cylinder is a series of tens display unit indexing teeth 146, each corresponding to an indicium on the tens display unit display surface 178. At one location of the internal surface of the hollow cylinder there is a zero stop means 180 in the form of an attached vertical solid cylindrical protrusion. The zero stop means serves to engage with a stop feature in the form of a corner 116 of the locating ledge 124 on the chassis 102 when the tens display unit 142 has reached its final position at the end of product life. In a preferred embodiment, tens indicia, e.g. in the form of a sequence of numerals "20", "19", . . . down to either "00" or "0" or a blank, are present. These numerals, and those of the units indicia, may advantageously be produced by hot foil printing, moulding, embossing, laser marking, or other suitable means.

The tens display unit 142 has a rim (FIG. 6) on its outermost edge which acts as a bearing surface whilst ensuring that the printed display cannot rub against the inside wall of the chassis 102. The tens display unit 142 is located centrally in the chassis 102 by the bearing rim on the outermost surface. It is located axially by a series of clip and location features 110, 124 on the chassis 102.

The tens display unit non-return arm 128 interacts with the tens display unit indexing teeth 146 and prevents rotation in the reverse direction and restricts rotation in the drive direction except when receiving an impulse from the tens display unit drive tooth 139 on the units display unit 133.

The tens display unit 142 has been designed such that it can be injection moulded without the requirement for a side action in the moulding tool. This is advantageous, as it will reduce the capital cost of tooling and reduce the risk of flash on components.

To assemble the dose counter 101, the units display unit 133 is mounted on the units display unit axle 118 on the chassis frame 104. The tens display unit 142 is then hooked under the tens display unit locating ledge 124 and pushed past the two tens display unit clips 110. Once assembled, the dose counter 101 can then be inserted into an actuator as an assembled unit.

FIGS. 8A and 8B show different perspective views of a third embodiment of a dose indicator 201, similar to the second embodiment shown in FIGS. 7A and 7B. It differs from the second embodiment by having a single spring arm 212 attached to the displacement plate 219 and located remotely from the hinges 220 and in close proximity to the drive pawl 206. The chassis displacement plate 219 is anchored to the chassis frame 204 by two hinges 220. The advantage of using a single spring arm 212 is that it will approximately halve the force required to actuate the dose indicator.

Figure 9A:
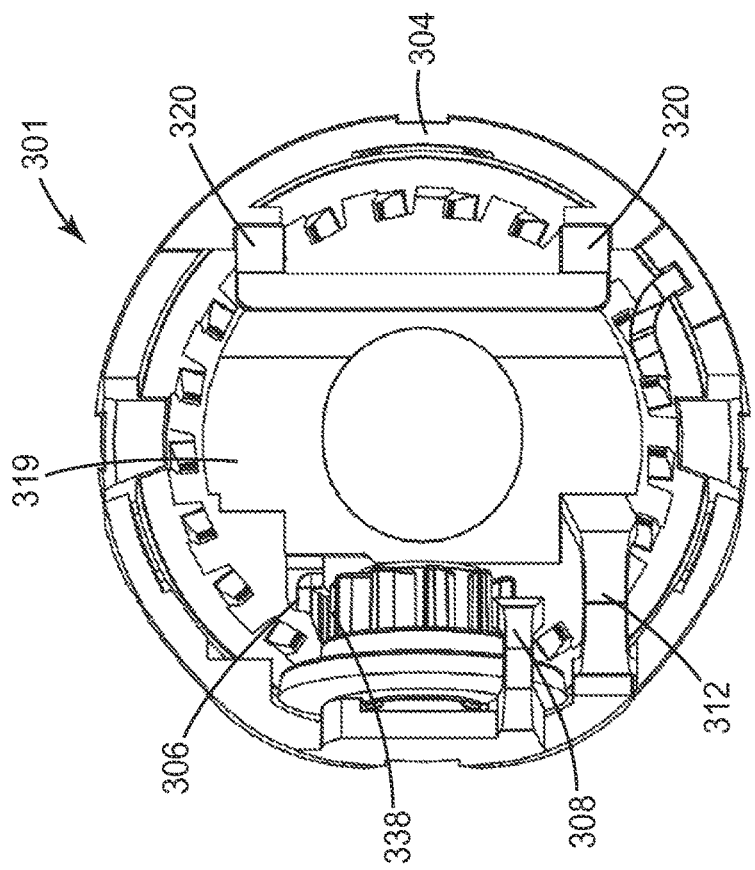
FIGS. 9A and 9B show different perspective views of a fourth exemplary dose indicator.
Figure 9B:
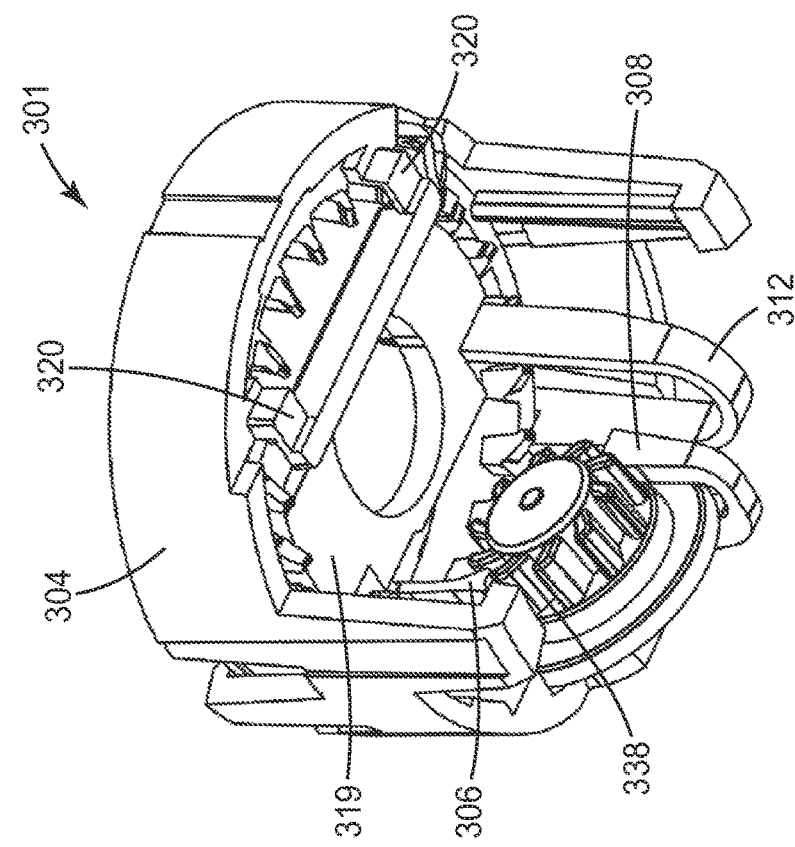

FIGS. 9A and 9B show different perspective views of a fourth embodiment of a dose indicator 301, similar to the second embodiment shown in FIGS. 7A and 7B. It differs from the second embodiment by having a single spring arm 312 attached to the displacement plate 319 and located remotely from the hinges 320 and on the same side of the dose indicator as the non-return arm 308, and thus located further from the drive pawl 306 than in the third embodiment. The chassis displacement plate 319 is anchored to the chassis frame 304 by the two hinges. This embodiment has a further advantage over the third embodiment that the displacement plate 319 will tend to yaw during actuation such that it increases the engagement of the drive pawl 306 with the indexing tooth 338.

The invention claimed is:

1. A dose indicator comprising,
a chassis comprising a chassis frame and a displacement portion,
an indexable first display unit, mountable on the chassis, the first display unit being indexable about a first display axis, the indexable first display unit comprising a plurality of indexing teeth,
a first display non-return arm, and
a drive pawl connected at its proximal part to the displacement portion, the drive pawl comprising:
a socket formed in its distal part, the socket being adapted to partially surround and engage a first indexing tooth of the first display unit during indexing, and
an outer surface connecting the proximal part and the distal part, the outer surface adapted to contact a second indexing tooth during resetting of the pawl after indexing.

2. The dose indicator as claimed in claim 1, wherein the distal part of the drive pawl comprises jaws, the inner surfaces of which define the socket.

3. The dose indicator as claimed in claim 1, wherein the drive pawl is resiliently displaceable by a displacement force from the subsequent indexing tooth during resetting of the pawl after indexing.

4. The dose indicator as claimed in claim 3, wherein the drive pawl and indexing teeth are adapted so that the displacement force is applied at a small displacement angle during resetting.

5. The dose indicator as claimed in claim 1, wherein the chassis further comprises at least one return mechanism.

6. The dose indicator as claimed in claim 5, wherein the return mechanism comprises at least one spring.

7. The dose indicator as claimed in claim 6, wherein the at least one spring comprises a leaf spring.

8. The dose indicator as claimed in claim 7, wherein the leaf spring comprises a curved leaf spring.

9. The dose indicator as claimed in claim 1, wherein each indexing tooth comprises a pawl engagement portion adapted to engage the socket.

10. The dose indicator as claimed in claim 1, wherein the non-return arm and the drive pawl both engage the same set of indexing teeth.

11. The dose indicator as claimed in claim 1, further comprising an indexable second display unit indexable about a second display axis, the second display axis being transverse to the first display axis.

12. The dose indicator as claimed in claim 11, wherein the first display unit and/or the second display unit are substantially circular and are rotatably indexable about the first display axis and/or about the second display axis respectively.

13. The dose indicator as claimed in claim 11, wherein the second display unit is a tens display unit.

14. The dose indicator as claimed in claim 11, wherein the first display unit comprises a drive arm adapted to index the second display unit.

15. The dose indicator as claimed in claim 11, wherein the second display unit has a substantially annular cross section.

16. The dose indicator as claimed in claim 1, wherein the chassis is moulded as a unitary piece.

17. The dose indicator as claimed in claim 1, wherein the drive pawl is integrally comprised in the displacement portion.

18. The dose indicator as claimed in claim 1, wherein the displacement portion is adapted to be displaced along a displacement path.

19. The dose indicator as claimed in claim 18, wherein the displacement path is at least partly transverse to the first display axis.

20. The dose indicator as claimed in claim 18, wherein the displacement path is at least partly arcuate.

21. The dose indicator as claimed in claim 1, wherein the displacement portion is mounted to the chassis frame by at least one hinge.

22. The dose indicator as claimed in claim 21, wherein the proximal part of the drive pawl is located on the displacement portion at a position remote from the at least one hinge at a position of the displacement portion distal to the at least one hinge.

23. The dose indicator as claimed in claim 21, wherein the at least one return mechanism directly or indirectly connects the displacement portion and chassis frame at a position remote from the at least one hinge.

24. The dose indicator as claimed in claim 1, wherein the displacement portion comprises at least one press member.

25. The dose indicator as claimed in claim 1, wherein the first display non-return arm is at least partly located on the chassis frame.

26. The dose indicator as claimed in claim 1, wherein the first and/or the second display unit is adapted to index through between 5 and 25 indicia.

27. The dose indicator as claimed in claim 26, wherein the first and/or the second display unit is adapted to index through between 8 to 12 indicia.

28. The dose indicator as claimed in claim 1, further comprising a first display unit mounting mechanism that mounts the display unit on the chassis frame so that it is indexable about the first display axis.

29. The dose indicator as claimed in claim 1, wherein the first display unit is a units display unit.

30. The dose indicator as claimed in claim 1, wherein the first display unit has a substantially circular cross section.

31. The dose indicator as claimed in claim 1, wherein the first and/or the second display unit comprises a zero stop member.

32. The dose indicator as claimed in claim 31, wherein the zero stop member interacts with a stop arm located on the chassis.

33. The dose indicator as claimed in claim 1, wherein the chassis comprises polyoxymethylene.

34. An actuator for an inhaler, the actuator comprising a dose indicator as claimed in claim 1.

35. An inhaler comprising an actuator as claimed in claim 34.

* * * * *